(12) United States Patent
Oonuma et al.

(10) Patent No.: US 9,709,585 B2
(45) Date of Patent: Jul. 18, 2017

(54) TRANSPORT LINE COVER

(71) Applicant: Hitachi High-Technologies Corporation, Tokyo (JP)

(72) Inventors: Mitsuru Oonuma, Tokyo (JP); Yoko Sato, Tokyo (JP); Hiroyuki Noda, Tokyo (JP); Shinji Azuma, Tokyo (JP); Naoto Tsujimura, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 14/577,379

(22) Filed: Dec. 19, 2014

(65) Prior Publication Data

US 2015/0175316 A1    Jun. 25, 2015

(30) Foreign Application Priority Data

Dec. 20, 2013    (JP) .................................. 2013-264575

(51) Int. Cl.
| | |
|---|---|
| *B65G 21/08* | (2006.01) |
| *B65G 21/00* | (2006.01) |
| *G01N 35/04* | (2006.01) |
| *G01N 35/00* | (2006.01) |

(52) U.S. Cl.
CPC ............. *G01N 35/04* (2013.01); *B65G 21/08* (2013.01); *G01N 2035/00277* (2013.01); *G01N 2035/00287* (2013.01); *G01N 2035/00326* (2013.01); *G01N 2035/0467* (2013.01)

(58) Field of Classification Search
None
See application file for complete search history.

(56) References Cited

U.S. PATENT DOCUMENTS

| | | | | |
|---|---|---|---|---|
| 5,161,678 A | * | 11/1992 | Garvey | ............. B65G 47/5145 198/347.4 |
| 5,947,266 A | * | 9/1999 | Rionde | ................. B65G 21/08 198/860.3 |
| 6,827,902 B1 | | 12/2004 | Kuriyama et al. | |

(Continued)

FOREIGN PATENT DOCUMENTS

| | | |
|---|---|---|
| CN | 1493510 A | 5/2004 |
| CN | 201385887 Y | 1/2010 |

(Continued)

OTHER PUBLICATIONS

Extended European Search Report, dated May 29, 2015, which issued during the prosecution of European Patent Application No. 14004099.9, which corresponds to the present application.

(Continued)

*Primary Examiner* — Kavel Singh
(74) *Attorney, Agent, or Firm* — Baker Botts L.L.P.

(57) ABSTRACT

A transport line cover with excellent workability that can be operated by an operator even with one hand. Proposed is a transport line cover that includes a cover body adapted to cover an opening at a top of a sample transport apparatus, the sample transport apparatus accommodating a plurality of transport lines that extend in one direction; and a first groove formed on an upper face of the cover body, the first groove extending from one short side to another short side of the cover body. A lower end of a long-side side face of the cover body is located at a level below a bottom face of the first groove.

10 Claims, 6 Drawing Sheets

(56) References Cited

U.S. PATENT DOCUMENTS

| | | | |
|---|---|---|---|
| 2002/0053529 A1 | 5/2002 | White | |
| 2005/0178770 A1* | 8/2005 | Hase | B65D 25/005 220/592.2 |
| 2012/0177547 A1 | 7/2012 | Fukugaki et al. | |

FOREIGN PATENT DOCUMENTS

| | | |
|---|---|---|
| CN | 102472765 A | 5/2012 |
| CN | 202518748 U | 11/2012 |
| CN | 203154099 U | 8/2013 |
| CN | 203173313 U | 9/2013 |
| JP | 2003-293494 A | 10/2013 |
| WO | WO 2006/029482 A1 | 3/2006 |
| WO | 2011/040197 A1 | 4/2011 |

OTHER PUBLICATIONS

Office Action, mailed May 5, 2016, which issued during the prosecution of Chinese Patent Application No. 201410795897.1, which corresponds to the present application.

Office Action, mailed Sep. 26, 2016, which issued during the prosecution of Chinese Patent Application No. 201410795897.1, which corresponds to the present application.

* cited by examiner

TRANSPORT LINE COVER

CLAIM OF PRIORITY

The present application claims priority from Japanese patent application JP 2013-264575 filed on Dec. 20, 2013, the content of which is hereby incorporated by reference into this application.

BACKGROUND

Technical Field

The present invention relates to a cover that covers an opening at the top of a sample transport apparatus that is suited to transporting samples between a plurality of sample inspection apparatuses (hereinafter also referred to as a "transport line cover").

Background Art

In recent years, a variety of types of sample inspection apparatuses have been introduced into hospitals and the like to promote automation of sample inspection. Examples of sample inspection apparatuses include sample processing apparatuses, biochemical analyzers, immunoassay apparatuses, and sample accommodating apparatuses. In addition, the sample inspection apparatuses include not only single-module apparatuses but also apparatuses that are obtained by combining a plurality of modules.

RELATED ART DOCUMENTS

Patent Documents

Patent Document 1: International Publication No. WO2011/040197A
Patent Document 2: JP 2003-293494 A

SUMMARY

By the way, a layout for installing a sample inspection apparatus or a sample transport apparatus may vary depending on the installation place or needs of customers. In particular, as sample transport apparatuses are now often customized in accordance with the installation place or the like, it has become more difficult to use common component parts. For example, it has become more difficult to use common transport line covers for avoiding entry of dust or dirt.

Further, a typical sample transport apparatus has two transport lines that are arranged in parallel in the long-side direction thereof, but a transport line cover that is necessary therefor has a too large horizontal width for an operator to grasp with one hand. Therefore, the operator usually grasps the transport line cover with two hands to perform an operation of attaching or detaching the cover. However, when workability is considered, it would be desirable that the transport line cover be grasped with one hand.

In order to solve the aforementioned problem, structures recited in the claims are adopted, for example. Although this specification includes a plurality of means for solving the aforementioned problem, there is provided, as one example, a transport line cover that includes a (1) cover body adapted to cover an opening at a top of a sample transport apparatus, the sample transport apparatus accommodating a plurality of transport lines that extend in one direction; and (2) a first groove formed on an upper face of the cover body, the first groove extending from one short side to another short side of the cover body. A lower end of a long-side side face of the cover body is located at a level below a bottom face of the first groove.

According to the present invention, a transport line cover that can be grasped by an operator even with one hand is implemented. Other problems, structures, and advantages will become apparent from the following description of embodiments.

DETAILED DESCRIPTION OF THE EMBODIMENTS

Hereinafter, embodiments of the present invention will be described with reference to the drawings. It should be noted that the embodiments of the present invention are not limited to those described below, and various modifications and variations are possible within the scope and spirit of the invention. In addition, in all drawings used for the description, identical members are denoted by identical reference numbers in principle, and repeated description thereof will be omitted.

[Exemplary Appearance of Sample Inspection System]

Figure 1:
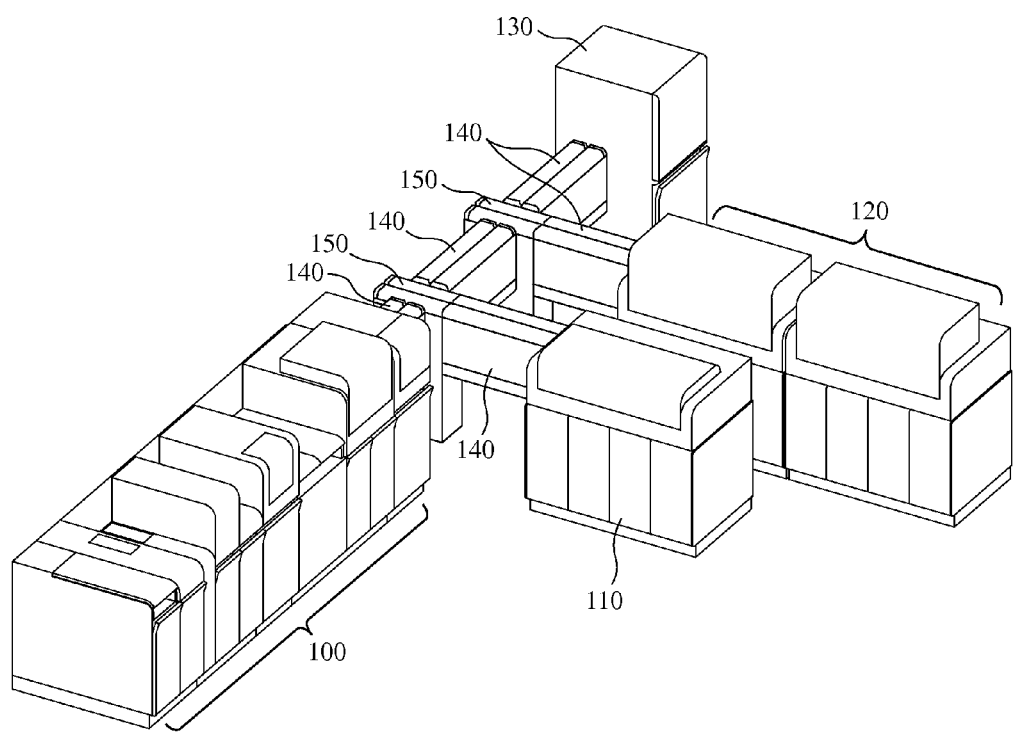
FIG. 1 is a perspective view showing the appearance structure of a sample inspection system.

FIG. 1 shows an exemplary appearance structure of a sample inspection system. The sample inspection system herein is an exemplary system that has a plurality of sample inspection apparatuses connected together with dedicated transport channels (i.e., sample transport apparatuses). The scale of the sample inspection system and the combination of sample inspection apparatuses that constitute the system may differ in accordance with the installation place or needs of customers. In this specification, a sample refers to a target to be inspected that is egested or taken from a human body, and includes, for example, blood, urine, feces, tissues, and cells.

The sample inspection system shown in FIG. 1 includes a sample processing apparatus 100, a sample analyzer (i.e., biochemical analyzer) 110, a sample analyzer (i.e., an apparatus obtained by connecting a biochemical analyzer and an immunoassay apparatus) 120, a sample accommodating apparatus (i.e., refrigerator) 130, five sample transport apparatuses 140, and two sample transport apparatuses 150 for connection.

The inspection processing apparatus 100 in this embodiment includes, for example, a loading module for installing a loaded sample onto an inspection rack (hereinafter referred to as a "sample holder"), a storage module for taking out the sample from the sample holder, a processing module (e.g., an centrifugal module, an uncapping module, a dispensing module, a barcode sticking module, or a sample classification module) for executing a predetermined process on the sample and/or the sample holder, a rack stocker for supplying and collecting sample holders, and a control unit (not shown). The sample processing apparatus 100 has extended main transport lines, each of which transports sample holders each holding at least one sample in the long-side direction, such that the main transport line crosses the module.

In this embodiment, main transport lines are arranged in two stages including upper and lower stages. In each stage, two main transport lines that transport samples in opposite directions are arranged in parallel. It should be noted that the main transport lines on the lower stage side are adapted to transport empty sample holders from which samples have been taken out. Needless to say, the main transport lines may also be arranged in a single stage or three or more stages. The specifications, such as the dimensions, mounting positions, and mounting heights of the main transport lines are made common to all apparatuses that constitute the sample inspection system (in the case of FIG. 1, the sample analyzer 110, the sample analyzer 120, the sample accommodating apparatus 130, the sample transport apparatuses 140, and the sample transport apparatuses 150 for junction).

It should be noted that the sample analyzer 110 is a stand-alone biochemical analyzer; the sample analyzer 120 is an apparatus obtained by connecting a biochemical apparatus and an immunoassay apparatus in series in the transport direction; and the sample accommodating apparatus 130 is a large-tower-type accommodating apparatus used for refrigeration storage of samples.

The sample transport apparatus 140 is a specialized transport apparatus for transporting samples and/or sample holders in the long-side direction, and basically has no other functional portions than the transport function. The sample transport apparatus 140 includes in its housing the aforementioned main transport lines, a drive mechanism (which includes a belt conveyor and its driving motor) for moving sample holders along the main transport lines, a power supply unit that supplies power to at least the motor and the like of the drive mechanism, and wires such as power lines and control signal lines.

Figure 2:
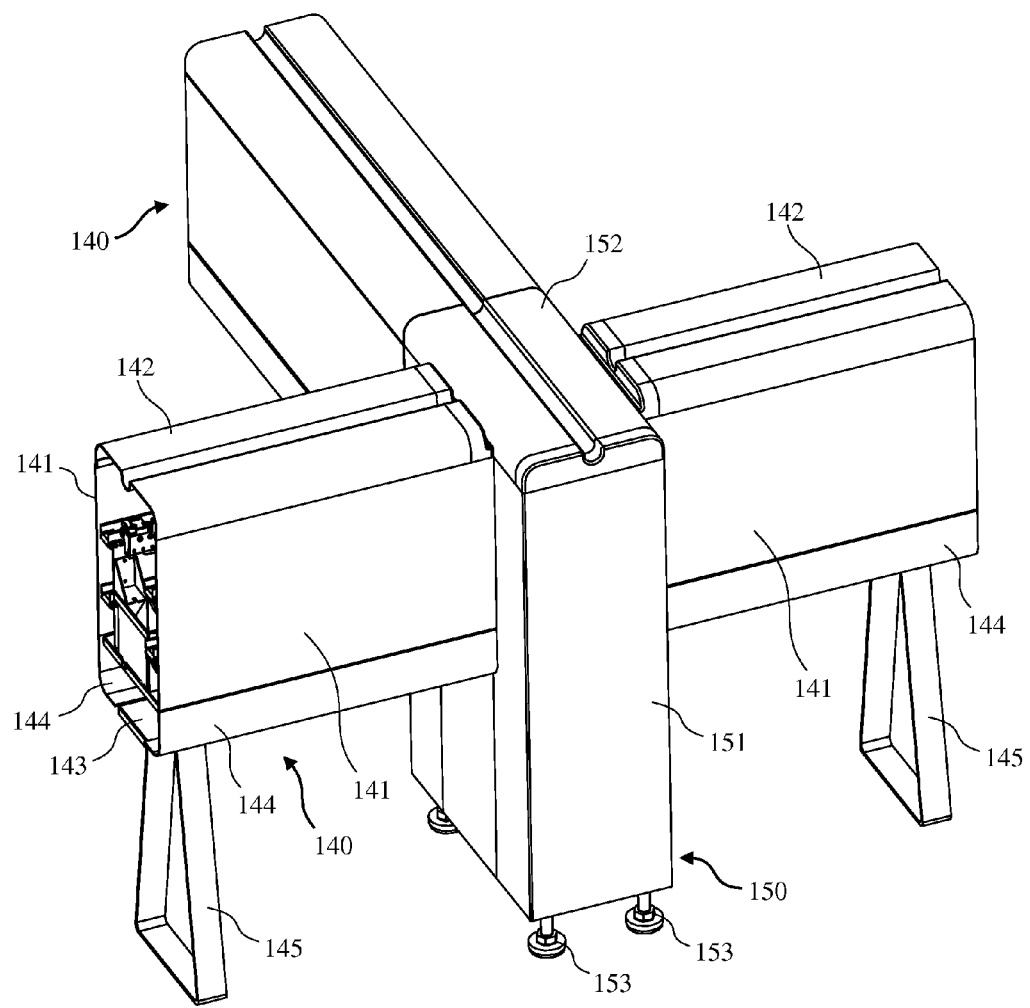
FIG. 2 is a view showing exemplary assembly of a sample transport apparatus.

FIG. 2 shows an exemplary appearance of the sample transport apparatus 140. In FIG. 2, the sample transport apparatus 140 is connected in a T-shape via the sample transport apparatus 150 for junction. The sample transport apparatus 140 shown in FIG. 2 accommodates transport lines that extend in the long-side direction, a pair of right and left housings (panels) 141 forming the long-side side faces, a transport line cover 142 that covers an opening at the top of the housings, a base substrate 143 that supports the housings 141 and an internal structure (not shown), openable/closable doors 144 forming the long-side side faces of the sample transport apparatus 140 together with the housings 141, and legs 145 attached to the bottom of the base substrate 143.

The sample transport apparatus 140 is based on the premise that it will be connected to another sample transport apparatus or a sample inspection apparatus, and thus has open opposite ends in the long-side direction. That is, the sample transport apparatus 140 has a cylindrical appearance whose cross section is approximately rectangular in shape. In this embodiment, one of two types of units that have common component parts other than the transport line length (that is, the length of the housing in the long-side direction) is used for the sample transport apparatus 140. In this embodiment, the transport line length is supposed to be 600 mm or 900 mm.

The sample transport apparatus 150 for junction is a transport-only apparatus that can connect to the sample transport apparatus 140 and/or the sample inspection apparatus in a plurality of directions. Therefore, as with the sample transport apparatus 140, the sample transport apparatus 150 for junction basically has no other functions than the transport function. Thus, the sample transport apparatus 150 for junction includes main transport lines, a drive mechanism (which includes a belt conveyor and its driving motor) that moves sample holders along the main transport lines, a power supply unit that supplies power to at least the motor and the like of the drive mechanism, and wires such as power lines and control signal lines.

However, the sample transport apparatus 150 for junction has, in addition to the transport mechanism for taking in and out sample holders to/from the sample transport apparatus 140 or a sample inspection apparatus, which is connected in series with the sample transport apparatus 150 for junction in the long-side direction, a transport mechanism for taking in and out sample holders to/from the sample transport apparatus 140 connected at a predetermined mounting angle, sub-transport lines for transferring sample holders from one of the pair of main transport lines arranged in parallel to the other main transport line, a stopper used to individually switch the transport directions of sample holders at a plurality of branch points in the transport direction, and a direction changing mechanism.

The sample transport apparatus 150 for junction comes in various shapes, for example, those for T-shape connection, L-shape connection, and Y-shape connection. The sample transport apparatus 150 for junction shown in FIG. 2 is the apparatus for T-shape connection. It should be noted that when transport to one of the sample transport apparatuses 140 that extend rightward and leftward from the long-side side faces of the sample transport apparatus 150 for junction is not necessary, the sample transport apparatus 150 for junction for L-shape connection is used. Needless to say, the sample transport apparatus 150 for junction for T-shape connection can also be used as a sample transport apparatus 150 for junction for L-shape connection as long as one of the two openings formed on the respective long-side side faces of the sample transport apparatus 150 for junction for T-shape connection is covered.

The sample transport apparatus 150 for junction includes a rectangular housing 151 for accommodating main-transport lines that extend in the long-side direction and sub-transport lines that extend in the short-side direction, and a transport line cover 152 that covers an opening at the top of the housing. In FIG. 2, the housing 151 of the sample transport apparatus 150 for junction is a box-shaped housing whose bottom face is near a floor surface (i.e., installation surface), and has four height adjustment legs 153 at the bottom face.

[Exemplary Structure 1 of Transport Line Cover]

Herein, a specific structure of the transport line cover 152 that is suitable for a use in which the transport line cover 152 covers an opening at the top of the sample transport apparatus 150 for junction for T-shape connection is shown. In this embodiment, the transport line cover 152 is assumed to be detachably mounted on the opening at the top. With the detachable transport line cover 152, it is possible to directly perform maintenance of the transport lines only by removing the transport line cover 152. Needless to say, the transport line cover 152 may also be integrally fixed to the opening at the top of the sample transport apparatus 150 for junction. Hereinafter, description will be made of a case where the transport line cover 152 is detachably mountable on the opening at the top.

The sample transport apparatus 150 for junction for T-shape connection is connected to other sample transport apparatuses 140 only on the two long-side side faces and one short-side side face as described with reference to FIG. 2. That is, it is unnecessary to consider connection of the remaining short-side side face to another sample transport apparatus 140. Therefore, a structure for avoiding entry of dust or dirt into the sample transport apparatus 150 for junction from the outside is adopted for the short-side side face to which another sample transport apparatus 140 need not be connected.

Figure 3A:
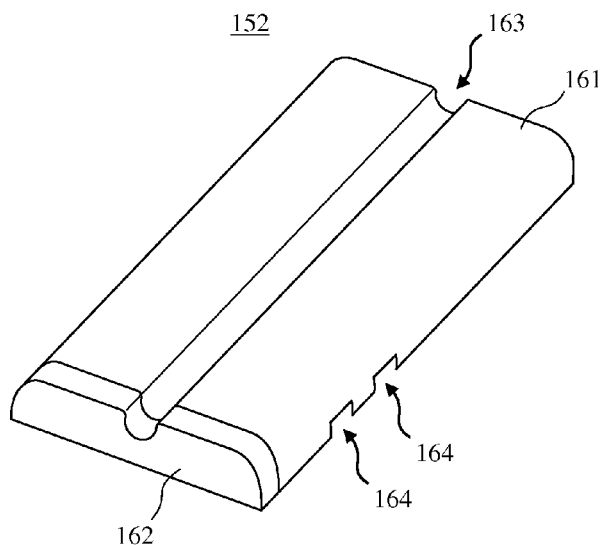
FIG. 3A is a perspective view showing an exemplary appearance of a transport line cover that is preferably used with one end thereof being at a position not connected to another sample inspection apparatus.
Figure 3B:
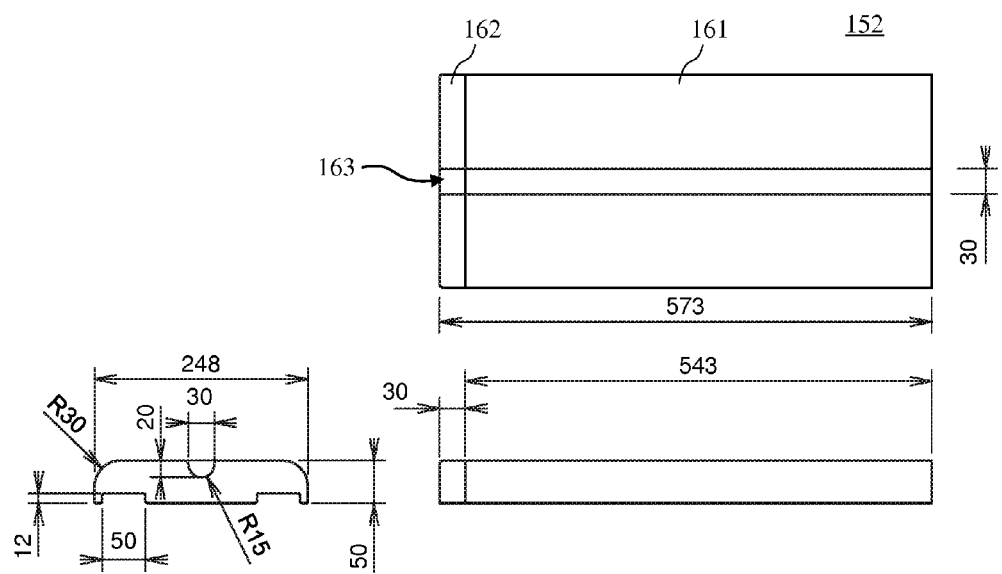
FIG. 3B is a view showing exemplary dimensions of the transport line cover shown in FIG. 3A.

FIGS. 3A and 3B each show an exemplary structure of the transport line cover 152. The transport line cover 152 includes a cover body 161 and an end cap 162 that is attached to an opening at one end (i.e., on a short-side side face) of the cover. The transport line cover 152 is designed in accordance with the dimensions of an opening at the top of the sample transport apparatus 150 for junction. FIG. 3B shows exemplary dimensions that are suitable for the transport line cover 152 of a 600 mm type. In the case of FIG. 3B, the length of the transport line cover 152 in the long-side direction is 573 mm. Herein, the length of the cover body 161 in the long-side direction is 543 mm, and the length of the end cap 162 in the same direction is 30 mm. In addition, the length of the transport line cover 152 in the short-side direction is 248 mm, and the height thereof is 50 mm.

The upper face of each of the cover body 161 and the end cap 162 has formed thereon a linear groove 163 that extends from one short side to the other short side of the transport line cover 152. Such groove 163 has a shape and position that allow an operator to easily grasp the transport line cover 152 with one hand. Specifically, the groove 163 is formed at a position where both the groove 163 and one long-side side face of the cover body 161 can be grasped with one hand. In this embodiment, the groove 163 is formed such that it passes through the center position of the transport line cover 152 in the short-side direction. Therefore, an operator is able to grasp the long-side side face on either the right side or the left side with respect to the groove 163. It should be noted that as the groove 163 is integrally formed such that it penetrates up to the opposite ends of the transport line cover 152 (i.e., across the entire region of from the cover body 161 up to an end of the end cap 162), it is possible to easily sweep dust and dirt, which have accumulated in the groove 163, away from both ends of the transport line cover 152. In addition, the groove 163 also has the effect of increasing the rigidity of the transport line cover 152.

The groove 163 in this embodiment is formed in a shape that allows at least the first joint of a finger to be inserted into the groove 163 from above the transport line cover 152. In the case of FIG. 3B, the length (width) of the groove 163 in the short-side direction is 30 mm, and the depth thereof from the upper face is 20 mm. The cross-sectional shape of the groove 163 may be any shape, for example, a rectangular shape, a U-shape, or a semicircular shape. FIG. 3B shows an example in which the cross-sectional shape of the groove 163 is a U-shape. When the groove 163 has a U-shaped cross-section, the groove 163 is formed by two upper inner wall portions that are opposite each other and one lower, curved inner wall portion that forms a bottom face. In the case of FIG. 3B, the height of each upper inner wall portion is 5 mm, and the lower, curved inner wall portion is formed along a semicircle with a radius of 15 mm.

In this embodiment, each upper inner wall portion of the groove 163 is formed at right angles to the upper faces of the cover body 161 and the end cap 162. Herein, a connection portion between the upper face and the long-side side face of each of the cover body 161 and the end cap 162 can also be formed in a similar shape. However, in this embodiment, the connection portion between the upper face and the long-side side face is formed such that the cross-sectional shape thereof is along a curved surface with a radius of 30 mm. Needless to say, such cross-sectional shape is only exemplary. Further, the radius that defines the connection portion is not limited to a constant value, and the radius of the curved face may continuously change along the direction from the side of the groove 163 toward the long-side side face.

Figure 4:
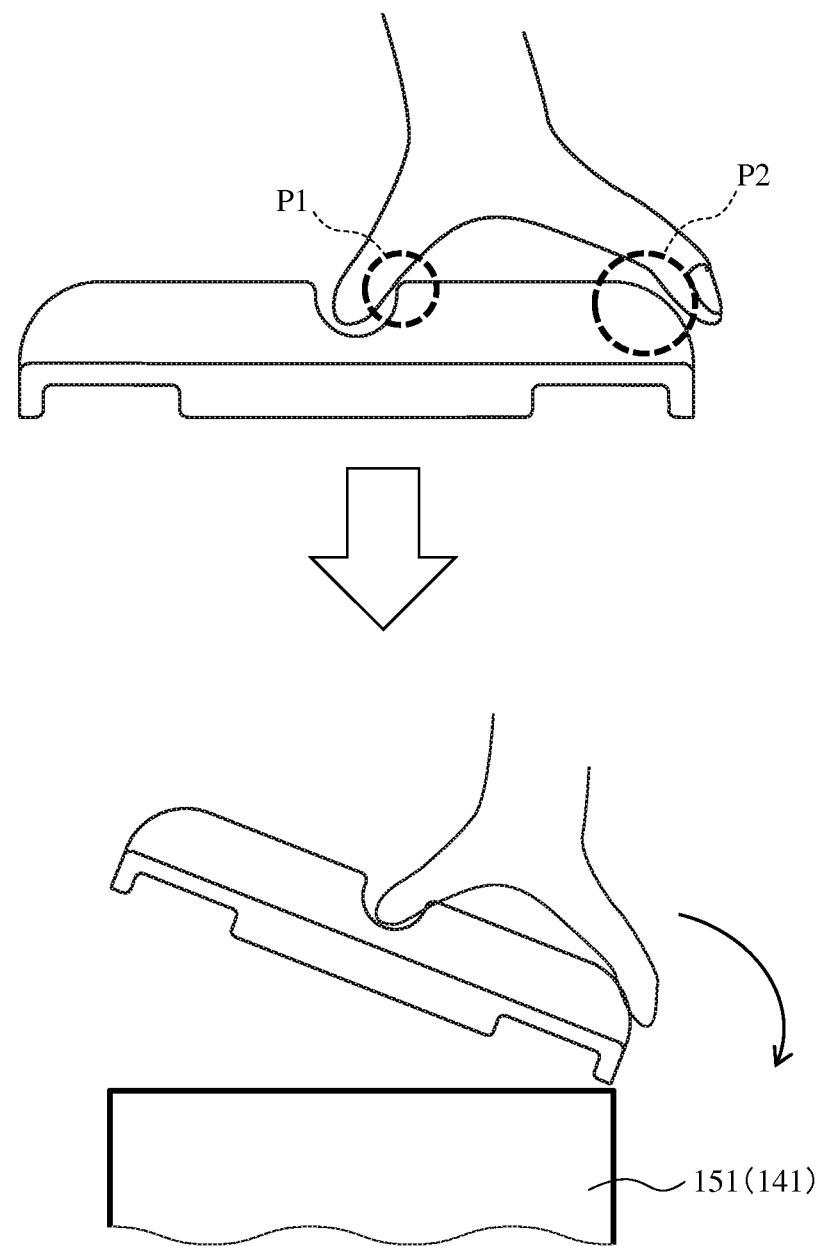
FIG. 4 is a view illustrating the relationship between the tilt angle of a point P1 and the tilt angle of a point P2.

In any case, a tilt angle that is formed between each upper inner wall of the groove 163 and the upper face is formed to be greater than a tilt angle that is formed at the connection portion between the upper face and the long-side side face of the cover body 161. The reason therefor will be described with reference to FIG. 4. In the case of FIG. 4, the angle of an edge portion (i.e., point P1) between the groove 163 and the upper face of the transport line cover 152 is a right angle, while the tilt angle of a connection portion (i.e., point P2) between the upper face and the long-side side face of the transport line cover 152 is gentle. That is, the angle of the point P2 is more gentle than the angle of the point P1.

When such a relationship is established, it will be easier for an operator to, when grasping the transport line cover 152 with one hand, apply a downward force to the point P2 with the point P1 as a support. Consequently, it will be easier for the operator to remove the transport line cover 152 by tilting the transport line cover 152 such that it becomes away from the opening at the top of the sample transport apparatus 150 for junction. Thus, it is possible to reduce the risk that the transport line cover 152 may fall in the opening at the top. Although FIGS. 3A, 3B and 4 each show an example in which the transport line cover 152 has a flat upper face, the transport line cover 152 may also have a dome-like cross-sectional shape or a hog-backed cross-sectional shape.

At least the cover body 161 of the transport line cover 152 in this embodiment is formed with a resin material (i.e., transparent resin). When the cover body 161 is formed with transparent resin, it is possible to observe or check the transport state of a sample or the state of the transport line portions from the outside. In addition, in this embodiment, two cutouts 164 are formed on a side face of the cover body 161. Such cutouts 164 are provided corresponding to the mounting positions of transport lines in the sample transport apparatus 140 connected from the lateral side. Thus, the transport line cover 152 for T-shape connection has two cutouts 164 on each of the two long-side side faces. Meanwhile, the transport line cover 152 for L-shape connection has two cutouts 164 only on one of the two long-side side faces to which another apparatus is connected.

The cutouts 164 herein are formed in order to avoid collision between samples, which are transported along transport lines, and the lower ends of the long-side side faces of the transport line cover 152. Thus, when there is no need to take such collision into consideration (i.e., when the upper face portions of samples travel at a height that is below the lower end of the transport line cover 152), the cutouts 164 need not be provided. It should be noted that in this embodiment, each cutout 164 has dimensions: a length of 50 mm and a height of 12 mm.

As described above, the cover body 161 has the end cap 162 attached to an opening at one end of the cover body 161. In this embodiment, the end cap 162 is attached such that it is embedded into the opening at one end of the body cap 161. The end cap 162 may be either removable from the cover body 161 or be unremovabley secured to the cover body 161.

[Exemplary Structure 2 of Transport Line Cover]

Next, a specific structure of the transport line cover 142 that is suitable for a use in which the transport line cover 142 covers an opening at the top of the sample transport apparatus 140 is shown. In this embodiment, the transport line cover 142 is also assumed to be detachably mounted on the opening at the top. Needless to say, the transport line cover 142 may also be integrally fixed to the opening at the top of the sample transport apparatus 140. Hereinafter, description will be made of a case where the transport line cover 142 is detachably mountable on the opening at the top.

Figure 5A:
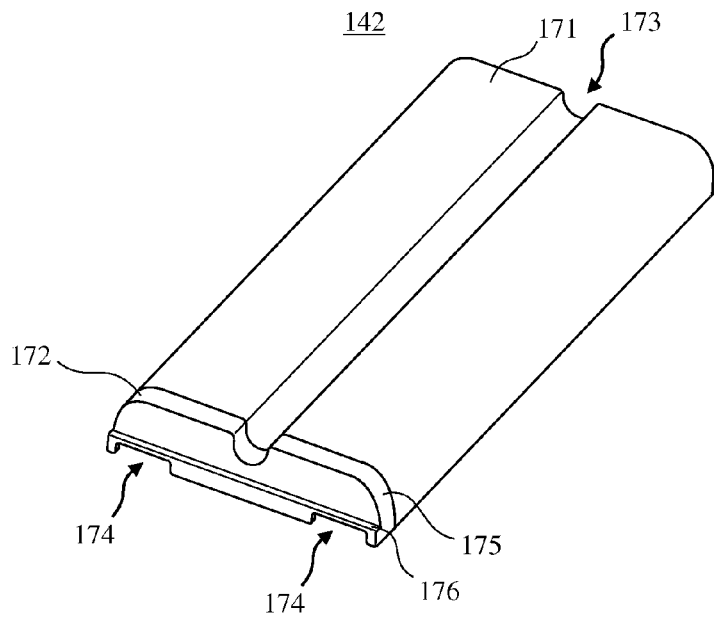
FIG. 5A is a perspective view showing an exemplary appearance of a transport line cover that is preferably used at a position connected to a sample transport apparatus for junction.
Figure 5B:
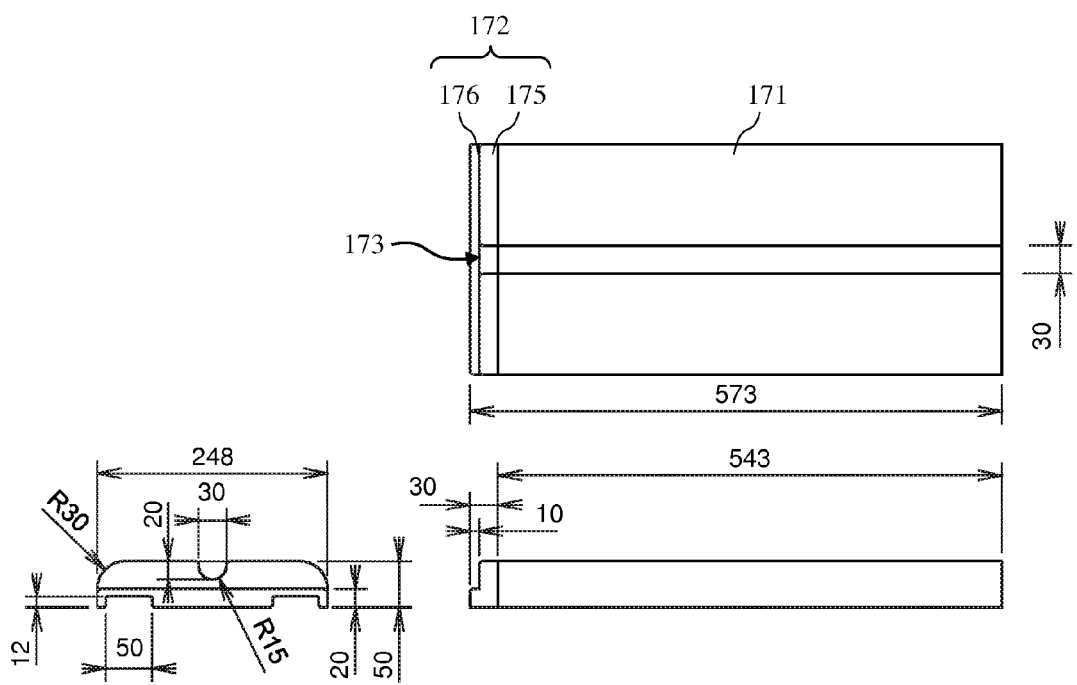
FIG. 5B is a view illustrating exemplary dimensions of the transport line cover shown in FIG. 5A.

FIGS. 5A and 5B each show an exemplary structure of the transport line cover 142 with an end cap. That is, FIGS. 5A and 5B each show an exemplary structure of the transport line cover 142 that is preferably used at a portion where the sample transport apparatus 140 is connected to the sample transport apparatus 150 for junction. The transport line cover 142 includes a cover body 171 and an end cap 172 that is attached to an opening at one end (i.e., on a short-side side face) of the cover. The transport line cover 142 is designed in accordance with the dimensions of an opening at the top of the sample transport apparatus 140. FIG. 5B shows exemplary dimensions that are suitable for the transport line cover 142 of a 600 mm type. In the case of FIG. 5B, the length of the transport line cover 142 in the long-side direction is 573 mm. Herein, the length of the main cover 171 in the long-side direction is 543 mm, and the length of the end cap 172 in the same direction is 30 mm. In addition, the length of the transport line cover 142 in the short-side direction is 248 mm, and the height thereof is 50 mm. It should be noted that in the case of the transport line cover 142 of the sample transport apparatus 140 that has no portion connected to the sample transport apparatus 150 for junction, the end cap 172 is not necessary. Thus, in such a case, the length of the cover body 171 in the long-side direction is 573 mm.

The transport line cover 142 also has a linear groove 173, which extends from one short side to the other short side of the transport line cover 142, formed on the upper faces of the cover body 171 and the end cap 172. The purpose of forming the groove 173, the dimensions thereof, and the like are similar to those of the aforementioned transport line cover 152. Thus, detailed description thereof is omitted herein. Hereinafter, the structure of the end cap 172 that is specific to the transport line cover 142 will be described.

The end cap 172 has formed therein an upper-stage portion 175 with a length of 20 mm in the long-side direction of the transport line cover 142, and a lower-stage portion 176 that further protrudes beyond the upper-stage portion 175 in the long-side direction by 10 mm. It should be noted that the amount of protrusion of the lower-stage portion 176 is determined so as to provide sufficient dimensions to allow a fingertip to be inserted to grasp the transport line cover 152 that is attached to the sample transport apparatus 150 for junction.

Figure 6:
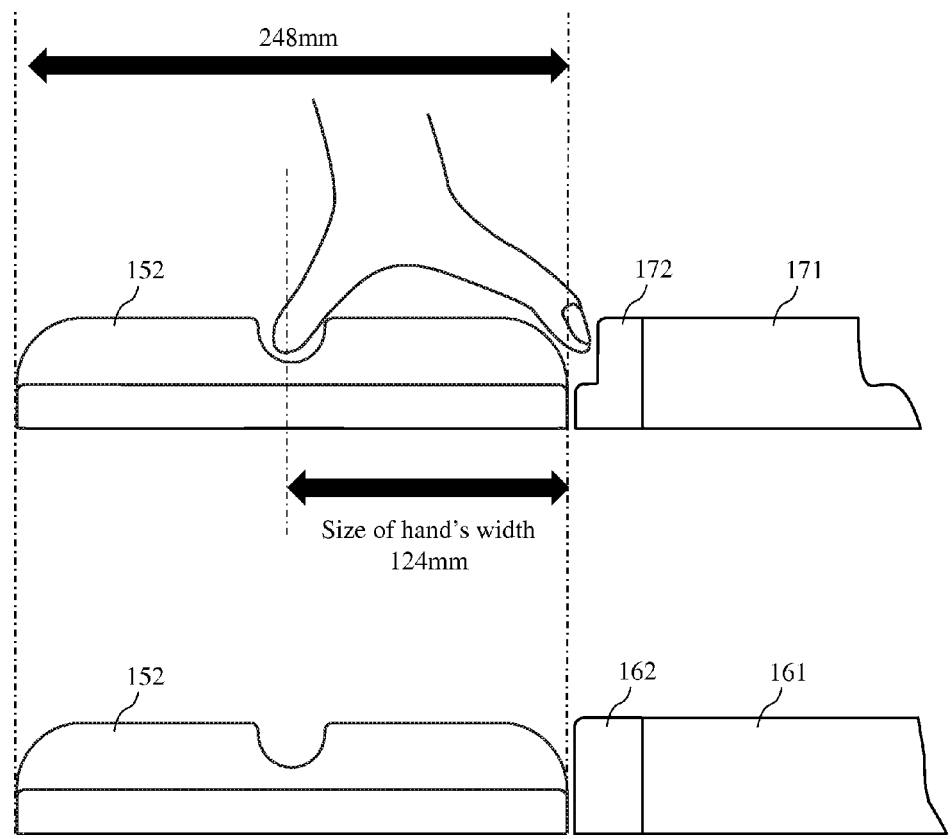
FIG. 6 is a view showing the advantage of using the transport line cover shown in FIGS. 5A and 5B.

When the end cap 172 is used, it is possible to, as shown in the upper view of FIG. 6, secure enough space for a fingertip to be inserted between the end cap 172 and the long-side side face of the transport line cover 152 by the amount of protrusion of the lower-stage portion 176, so that the transport line cover 152 can be grasped with one hand even at a portion where the sample transport apparatus 150 for junction is connected to the sample transport apparatus 140. Provided that the end cap 172 has no lower-stage portion, it would be impossible to, as shown in the lower view of FIG. 6, secure enough space for a fingertip to be inserted between the end cap 162 and the long-side side face of the transport line cover 152, so that it would be impossible for the transport line cover 152 to be grasped with one hand at a portion where the sample transport apparatus 150 for junction is connected to the sample transport apparatus 140.

The height of the lower-stage portion 176 in this embodiment is 20 mm. It should be noted that the height of the lower-stage portion 176 is not limited to 20 mm as long as it is lower than the height of the bottom of the groove 173. In this embodiment, the height of the bottom of the groove 173 is 30 mm in the upward direction from the lower face of the end cap 172 (or 20 mm in the downward direction from the upper face). Thus, it is acceptable as long as the height of the lower-stage portion 176 is less than 30 mm. Needless to say, as the height of the lower-stage portion 176 is greater, the space for inserting a finger becomes narrower, with the result that the transport line cover 152 becomes difficult to grasp. Thus, the height of the lower-stage portion 176 is desirably as low as possible.

It should be noted that when the two cutouts 174 for transporting samples are formed in the lower-stage portion 176 of the end cap 172 as shown in FIG. 5A, the lower limit of the height of the lower-stage portion 176 is restricted by the heights of the cutouts 174. However, as described above, when there is no problem with transport of samples without providing the cutouts 174, the cutouts 174 need not be provided.

CONCLUSION

As described above, in this embodiment, two common lengths of transport lines that are 600 mm and 900 mm are prepared. Therefore, the types of the transport line covers 142 and 152 that should be prepared to cover an opening at the top of a sample transport apparatus can be significantly reduced, whereby it also becomes possible to reduce the production cost in comparison with a case where a dedicated cover should be produced each time.

Further, in this embodiment, the grooves 163 and 173 are formed on the upper faces of the transport line covers 152 and 142, respectively, such that the grooves extend from one short sides to the other short sides of the respective covers. Thus, it is possible to allow one inner wall of each groove and one long-side side face of each cover body to be grasped with one hand, and thus allow each of the transport line covers 142 and 152 to be attached to and detached from the opening at the top of the sample transport apparatus with one hand.

In addition, as a tilt angle that is an angle between the upper face of the transport line cover 142 or 152 and the groove 173 or 163 is formed to be greater than a tilt angle that is an angle between the upper face and the long-side side face of the transport line cover 142 or 152, it becomes possible to more easily remove each of the transport line covers 142 and 152 outwardly from the sample transport space. Consequently, the risk that the transport line cover 142 or 152 may fall in the transport space during an operation of removing the cover can be reduced. In addition, as the grooves 163 and 173 are formed such that they include the center positions of the transport line covers 152 and 142 in the short-side directions, respectively, it is possible to allow the transport line covers 142 and 152 to be grasped either on the right side or the left side with respect to the grooves 173 and 163, respectively.

In this embodiment, the end cap 172 of the transport line cover 142, which is used at least at a portion where the sample transport apparatus 140 is connected to the sample transport apparatus 150 for junction, is provided with the lower-stage portion 176, and the amount of protrusion of the lower-stage portion 176 is made greater than at least the length that allows a fingertip to be inserted. Thus, it is possible to allow the transport line cover 152 to be grasped with one hand even at a portion where the sample transport apparatus 140 is connected to the sample transport apparatus 150 for junction.

OTHER EMBODIMENTS

It should be noted that the present invention is not limited to the structures of the aforementioned embodiments, and includes a variety of variations. For example, the aforementioned embodiments are only some of embodiments described in detail to clearly illustrate the present invention, and thus can be similarly applied to other embodiments. For example, although the aforementioned embodiments illustrated examples of transport line covers for a case where the transport line length is 600 mm, a similar structure can also be adopted for a case where the transport line length is 900 mm.

In addition, the present invention need not include all of the structures described in the aforementioned embodiments. It is also possible to replace a part of a structure of any of the aforementioned embodiments with another structure. In addition, it is also possible to add, to a structure of any of the aforementioned embodiments, a structure of another embodiment. Further, it is also possible to remove a part of a structure of any of the aforementioned embodiments.

DESCRIPTION OF SYMBOLS

142 Transport line cover
152 Transport line cover
161 Cover body
162 End cap
163 Groove
164 Cutout
171 Cover body
172 End cap
173 Groove
174 Cutout
175 Upper-stage portion
176 Lower-stage portion

What is claimed is:

1. A transport line cover comprising:
a cover body adapted to cover an opening at a top of a sample transport apparatus, the sample transport apparatus accommodating a plurality of transport lines that extend in one direction;
a first groove formed on an upper face of the cover body, the first groove extending from one short side to another short side of the cover body, wherein a lower end of a long-side side face of the cover body is located at a level below a bottom face of the first groove; and
an end cap, the end cap being attachable to one of opposite ends of the cover body in a long-side direction, wherein an upper face of the end cap has formed thereon a second groove, the second groove extending from one short side to another short side of the end cap, and the second groove is integrally connected to the first groove in a state in which the end cap is attached to the cover body.

2. The transport line cover according to claim 1, wherein the first groove is adapted to be grasped with one hand together with one long-side side face of the cover body.

3. The transport line cover according to claim 1, wherein the first groove has a rectangular shape, a U-shape, or a semicircular shape when a short side of the cover body is seen from outside.

4. The transport line cover according to claim 1, wherein a first tilt angle that is an angle between the upper face of the cover body and the first groove is greater than a second tilt angle that is an angle between the upper face and the long-side side face of the cover body.

5. The transport line cover according to claim 1, wherein the cover body is attachable to and detachable from the opening at the top of the sample transport apparatus.

6. The transport line cover according to claim 1, wherein the cover body is formed of a transparent member.

7. The transport line cover according to claim 1, wherein the first groove includes a center position of the cover body in a short-side direction.

8. The transport line cover according to claim 1, wherein the end cap is attached such that the end cap is embedded into an opening at an end of the transport line cover.

9. The transport line cover according to claim 1, wherein the end cap arranged on a side in contact with a long-side side face of another transport line cover has a lower-stage portion, the lower-stage portion protruding in the long-side direction of the cover body beyond an upper-stage portion in which the second groove is formed.

10. The transport line cover according to claim 9, wherein the lower-stage portion has at least an amount of protrusion with dimensions that allow a fingertip to be inserted to grasp the other transport line cover.

* * * * *